United States Patent [19]

Hilverda

[11] Patent Number: Plant 7,413

[45] Date of Patent: Jan. 1, 1991

[54] CARNATION NAMED HILTINY

[75] Inventor: Jan J. Hilverda, Aalsmeer, Netherlands

[73] Assignee: Hilverda b.v., Netherlands

[21] Appl. No.: 308,646

[22] Filed: Feb. 10, 1989

[51] Int. Cl.[5] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new carnation cultivar particularly distinguished by its relatively short plant height and its profuse production of very small, generally magnolia purple flowers having a ruby red heart and borne in clusters on strong, erect, but relatively short flowering stems emitted near the soil and reaching a height of about 20 cm., the plant itself having a height of about 20 to 25 cm. with abundant foliage and a shape particularly adapted to pot plant culture.

1 Drawing Sheet

BACKGROUND OF THE NEW PLANT

This new carnation variety originated as a seedling of a hybrid resulting from my crossing a pair of unnamed and unpatented carnation varieties selected by me from my collection of carnation plants maintained by me for breeding purposes at my nursery in Aalsmeer, The Netherlands, the object of this crossing being to develop new plants which would improve the range of carnation varieties for commercial production by having a more rapid growth habit, new flower colors and improved production rate. This particular seedling was selected by me for propagation because of the light magnolia purple color of the flower petals, each of which is particularly distinguished by having a ruby red heart at its base and also because the plant itself had a rapid growth rate and reached a terminal height of only about 25 cm., which appeared to me to be an ideal subject for pot plant culture. This new plant was propagated by me at Aalsmeer by means of cuttings with such very satisfactory results that I promptly directed that this particular variety be propagated through several successive generation, by means of cuttings, to determine whether its distinctive characteristics would hold true from generation to generation and so that its homogenetic character could be assured for commercial production.

DESCRIPTION OF THE DRAWING

My new spray carnation cultivar is illustrated by the accompanying photographic drawing which shows, in full color, the upper end of a flowering stem, as well as a full face view of a mature flower, a bud and several of the petals, the colors shown being as nearly true as is reasonably possible to obtain by conventional photographic procedures.

DESCRIPTION OF THE NEW PLANT

The following is a detailed description of my new spray carnation cultivar based upon observation made during the current year at Aalsmeer, the color designations being according to The R.H.S. Colour Chart published by The Royal Horticultural Society of London, England.

THE PLANT

Origin: Seedling.

Parentage:

*Seed parent.*—An unnamed and unpatented carnation variety.

*Pollen parent.*—An unnamed and unpatented carnation variety.

Both of these varieties having been selected by me from my collection of many types and variations of carnation plants maintained by me at Aalsmeer for breeding purposes.

Classification:

*Botanic.*—*Dianthus carophyllus* L.

*Commercial.*—Pot Carnation.

Form: A short, erect bush.

Height: 20 to 25 cm.

Growth: Vigorous, strong and upright.

Branching character: Alternate.

Foliage:

*Quantity.*—Abundant and dense because of the short stature of the plant.

*Leaf size.*—About 6 to 8 cm. long.

*Leaf shape.*—Elliptic with entire margins and an acute tip.

*Texture.*—Leathery.

*Color.*—Blue Green for both upper and under sides.

*Leaflets.*—None.

*Ribs and veins.*—The midrib is prominent.

THE BUD

Size: Small.

*Diameter.*—About 5 to 8 mm.

*Length.*—Approximately 20 mm.

Form: Cylindrical.

Opening rate: With mature buds, the flower petals show in about three to four days.

Color of petals:

*When sepals first divide.*—Pink (Magnolia Purple).

*When petals begin to unfurl.*—Magnolia Purple with Ruby Red centers.

Sepals:

*Number.*—Five.

*Shape.*—Long ovate with acute apex.

*Character.*—The sepals are hooded over the bud before dividing and stand up as the flower petals unfurl.

*Color.*—Inside: White to light green. Outside: Dark green.

*Striae.*—None.

Calyx:
*Shape.*—Cylindrical.
*Size.*—Long.
*Splitting.*—The calyx does not split.
*Aspect.*—Smooth.
Flower stem:
*Length.*—About 20 cm.
*Character.*—Rigid and erect.
*Color.*—Dark green.

THE FLOWER

Blooming habit: Continuous and profusely.
Size of bloom: Quite small.
*Diameter.*—About 30 mm.
*Depth.*—About 10 to 12 mm.
Borne: In a cluster at the upper portion of a short, erect flowering stem.
Flower shape: When bloom first opens, it has a high center. When bloom matures, it tends to flatten.
Petalage:
*Number of petals.*—7 to 10.
*Arrangement.*—Imbricated.
*Form.*—Fan-shaped with rounded and dentated margins.
*Texture.*—Soft.
*Color.*—All petals: Magnolia Purple body, R.H.S. 70C, with a Ruby Red base, R.H.S. 59A.
*Petaloids:* None.
Flower stem:
*Length.*—About 20 cm.
*Character.*—Sturdy and upright.
*Color.*—Dark Green.
Discoloration after full bloom: None.
Persistence: The flowers hang on and dry.

Fragrance: Weak.
Lasting quality: On the plant, 14 to 21 days.

REPRODUCTIVE ORGANS

Stamens:
*Number.*—6 to 8.
*Arrangement.*—Evenly around the ovary.
*Anthers.*—Size: Small. Color: Cream White.
*Filaments.*—Length: About 10 to 12 mm. Color: White.
*Pollen.*—Color: White.
Pistils:
*Number.*—One.
*Style.*—Length: About 15 to 20 mm. Color: White.
*Stigma.*—Color: White.
Character of ovaries: Normal.

THE FRUIT

Fertility: The Fruit is fertile.
Shape: Lozenge-shaped.
Color at maturity: Yellow/Brown.

This new carnation variety most nearly resembles the pot carnation named 'Pinki' but is distinguished from 'Pinki' by its color, its more compact growth and higher flower production.

I claim:

1. The new and distinct carnation variety, substantially as herein shown and described, characterized by its short, bushy plant form and its small magnolia purple flowers, the petals of which each have a large ruby red heart at the midportion of the petal body and above the petal stem.

* * * * *

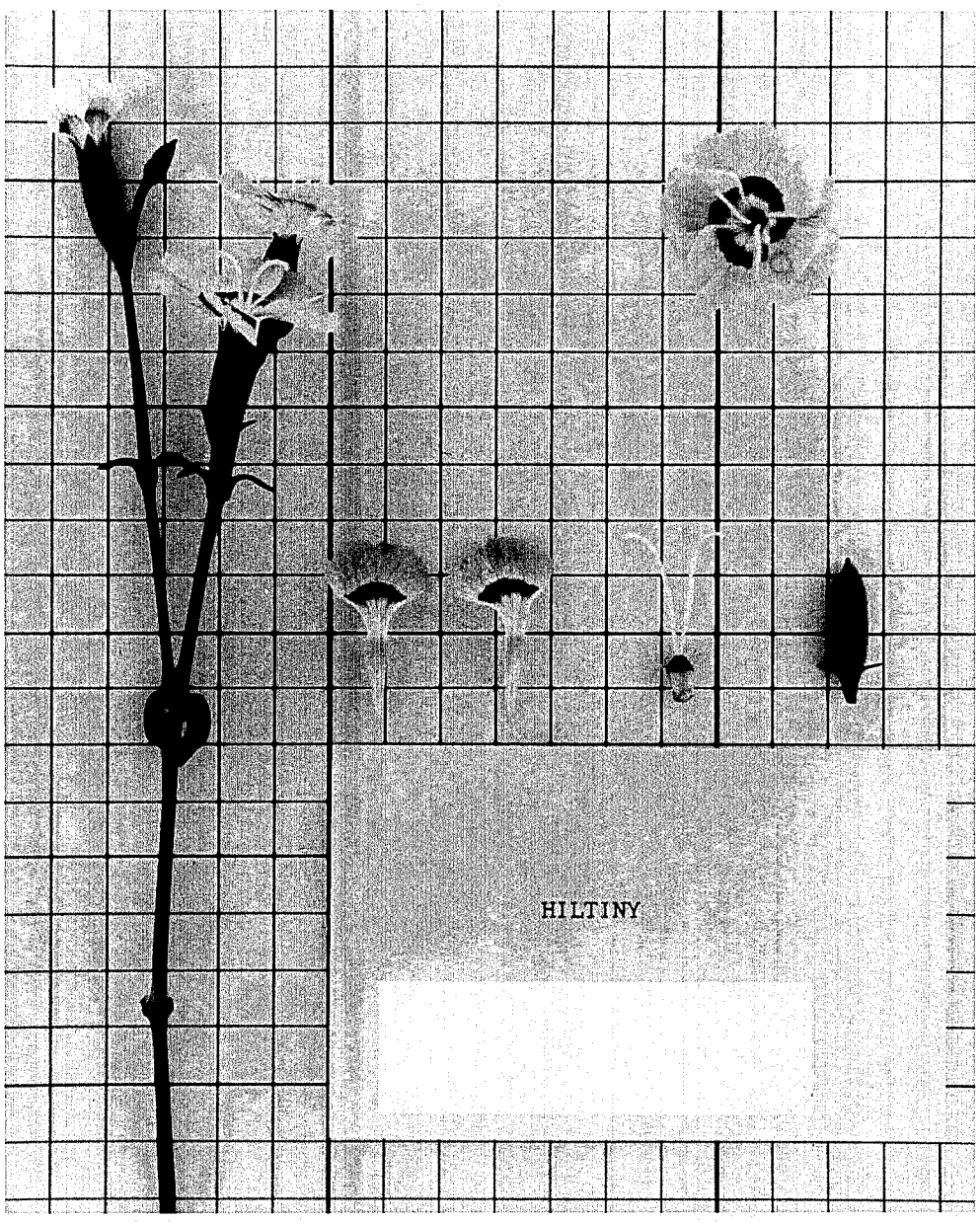
HILTINY